Figure 1:
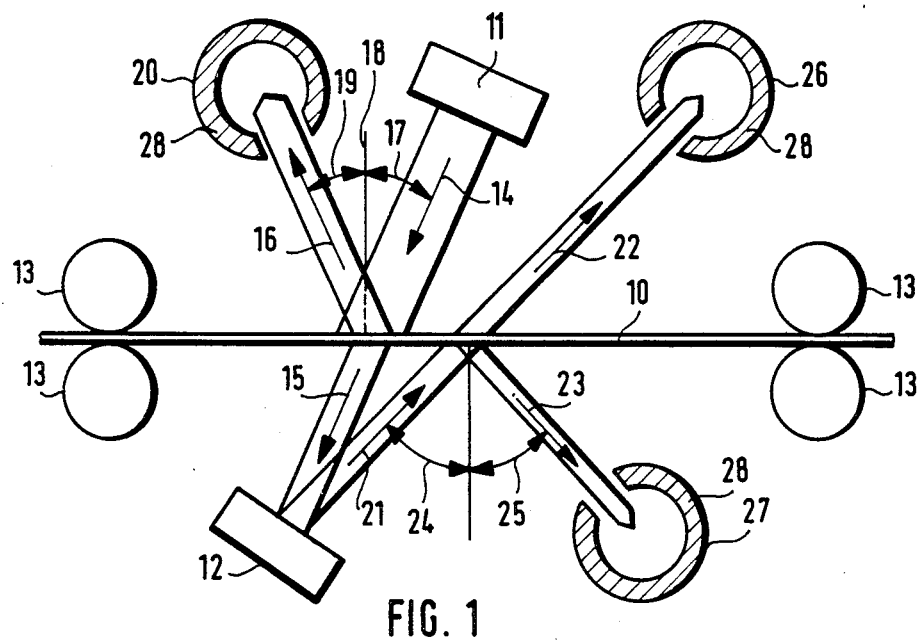

United States Patent [19]
Wunderer

[11] Patent Number: 4,612,807
[45] Date of Patent: Sep. 23, 1986

[54] APPARATUS FOR DETERMINING THE WEIGHT PER UNIT AREA OF SHEET-LIKE MATERIAL

[75] Inventor: Bernd Wunderer, Munich, Fed. Rep. of Germany

[73] Assignee: GAO Gesellschaft für Automation and Organisation mbH, Fed. Rep. of Germany

[21] Appl. No.: 671,858

[22] Filed: Nov. 15, 1984

[30] Foreign Application Priority Data

Jul. 4, 1984 [DE] Fed. Rep. of Germany ....... 3424652

[51] Int. Cl.$^4$ ........................................... G01N 29/00
[52] U.S. Cl. ....................................... 73/580; 73/159
[58] Field of Search ................. 73/580, 159, 627, 644

[56] References Cited

U.S. PATENT DOCUMENTS

| 2,912,854 | 11/1959 | Schubring | 73/627 |
| 2,984,756 | 5/1961 | Bradfield | 73/644 |
| 3,470,734 | 10/1969 | Agdur et al. | 73/580 |
| 3,624,712 | 11/1971 | Weighart | 73/627 |

FOREIGN PATENT DOCUMENTS 738941 10/1955 United Kingdom ................. 73/644

Primary Examiner—Anthony V. Ciarlante
Attorney, Agent, or Firm—Andrus, Sceales, Starke & Sawall

[57] ABSTRACT

The invention relates to an apparatus for dynamically determining the local weight per unit area of sheet-like material, for example, paper, in which the sheet-like material is exposed to sound waves from a sound transmitter. The portion of sound transmitted and/or reflected by the sheet-like material is measured by aid of a receiver and the weight per unit area determined from the measuring signal. In order to avoid disturbances of the measuring signal due to superimposed sound waves and in order to obtain high local resolution even in the case of quickly moving material to be measured, the transmitter, material to be measured and possibly the receiver as well are arranged on a slant relative to each other in such a way that the portions of sound reflected on these elements are faded out of the path of rays between the transmitter and the receiver. Means are additionally provided to prevent the faded out portions of sound from returning to the path of rays between the transmitter and the receiver.

9 Claims, 5 Drawing Figures

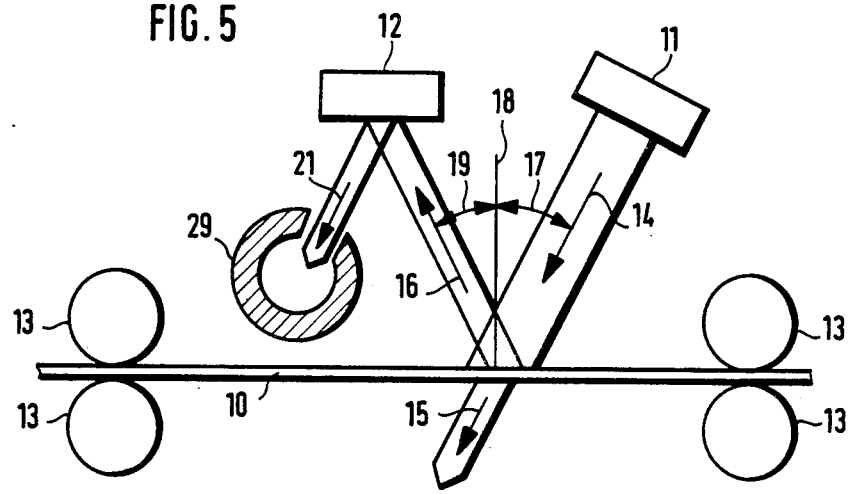

ical pulse, requires a certain time, depending on its band width, before it dies out and can be triggered again. This time is generally longer than the time interval of the receiver so that there is dead time, during which no measuring signal is present, between the intervals available for measuring. In the case of non-stationary measurement, for example when a sheet of paper, as the material to be measured, is moved past the transmitter-receiver arrangement, the local resolution of the known apparatus is dependent upon the dead time, or the pulse repetition frequency. When the speed of the material to be measured increases, small local deviations of the weight per unit area can therefore only be resolved to a limited extent.

APPARATUS FOR DETERMINING THE WEIGHT PER UNIT AREA OF SHEET-LIKE MATERIAL

The present invention relates to an apparatus for dynamically determining the local weight per unit area of sheet-like material, for example, paper, with which the sheet-like material is subjected to sound waves from a sound transmitter, the portion of sound transmitted and/or reflected by the sheet-like material is measured by aid of a receiver and the weight per unit area determined from the measuring signal.

German Offenlegungsschrift No. 15 48 170 discloses a device for measuring the weight per unit area of sheet-like material. The material to be measured is exposed to supersonics and the transmitted or reflected supersonic energy measured. The supersonic transmitter works continuously or in pulsed mode. In order to avoid disturbing superposition of sound waves, which may lead to stationary waves and echo formation, the housing receiving the transmitter and receiver is lined with sound-absorbing material. This measure allows the reflections on the housing wall to be suppressed, but it is disadvantageous in that single or multiple reflection can still occur on the transmitter, receiver and material to be measured. The reflection on the material to be measured may lead to considerable falsification of the measuring value in particular when the thickness of paper is being measured, since in the case of paper only a very small portion of the transmitter sound wave is transmitted by the paper, while a much larger portion is reflected and superimposes the transmitter sound wave.

In order to avoid errors during the determination of weight per unit area which may occur due to reflection on the transmitter, receiver and material to be measured, it is proposed in German Offenlegungsschrift No. 30 48 710 to control the transmitter in pulsed mode and activate the receiver only for a brief time interval. The time interval is set in such a way that the receiver is only switched on when the primary sound of the transmitter arrives, and is switched off as soon as the first systematic disturbances (reflections) occur. The transmitter, which is triggered by a short electr The invention is thus based on the problem of proposing an apparatus for determining the weight per unit area of sheet-like material, with which disturbances of the measuring signal due to the superposition of sound waves can be avoided and high local resolution can be attained in particular when the material to be measured is moved quickly relative to the transmitter-receiver arrangement.

The problem is solved according to the invention by the features stated in the characterizing part of the main claim.

The basic idea of the invention is to arrange all elements involved in measuring, such as the transmitter, receiver and material to be measured, in such a way that the portions of sound reflected on these elements are faded out of the path of rays between the transmitter and the receiver and at the same time the faded out portions of sound are prevented from returning to the original path of the rays and hitting the transmitter and/or receiver. This basic idea may be realized, for example, by arranging the material to be measured, not parallel, but at an angle to the transmitter and receiver and eliminating the sound reflected on the material to be measured by a sound-absorbing material.

European Offenlegungsschrift No. 00 98 115 does disclose an apparatus in which the transmitter and receiver are arranged on a slant to the material to be measured, but this apparatus is not suitable for solving the problems on which the present invention is based.

Since there cannot be any disturbing superposition of sound waves at any time in the path of rays between the transmitter and the receiver due to the inventive arrangement, the time at which the measurement takes place and any time interval in the receiver or the pulse repetition frequency do not have any effect on the measuring signal. The above-mentioned values can thus be adapted at will to the particular conditions at hand.

It is also possible, in particular, to work with continuous waves, i.e. with a transmitter sound wave which is radiated continuously. The use of continuous waves provides the advantage that there is no dead time, so that continuous measurement is possible. This allows for high local resolution to be attained in the direction of movement of the material to be measured, even when this material is moved past the transmitter-receiver arrangement quickly.

A further advantage of the inventive arrangement of the elements is that the position of the material to be measured relative to the transmitter and the receiver does not have any influence on the measuring signal. In the case of the known apparatus with the material to be measured arranged parallel to the transmitter and receiver, there are generally transmission changes when the material to be measured is moved in the direction of the connecting axis between the transmitter and the receiver. This undesirable effect comes about due to interference phenomena of the reflected sound waves, the transmission fluctuating in accordance with the phase relation of the interfering sound waves. This disadvantage is eliminated by the proposed solution, which has a positive effect in particular when the position of the material to be measured relative to the transmitter and receiver cannot be kept constant, for example when the material to be measured tends to flutter when moved quickly.

Further advantages and developments of the invention can be found in the subclaims as well as in the following description of embodiments of the invention with reference to the enclosed drawings.

Figure 2:
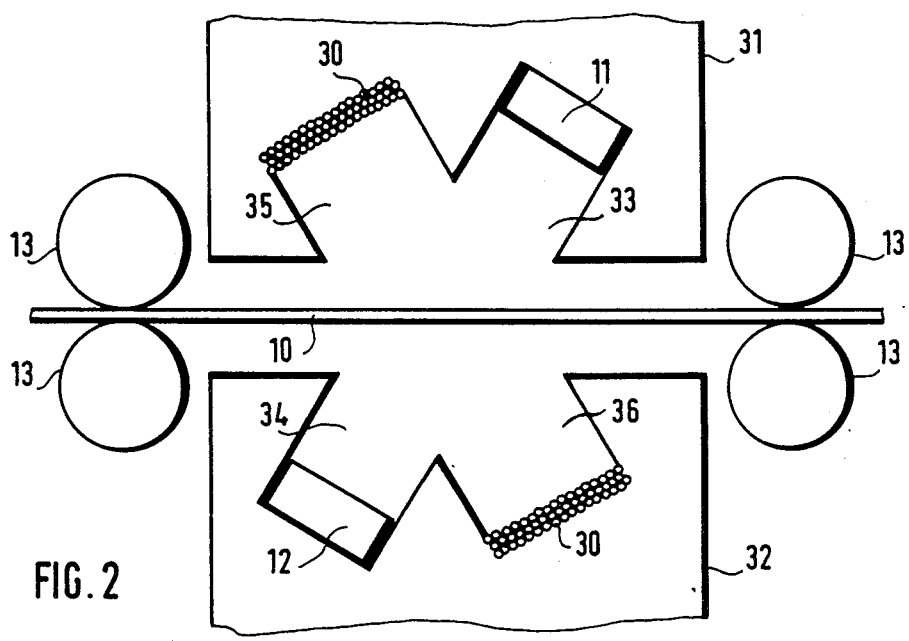
Figure 3:
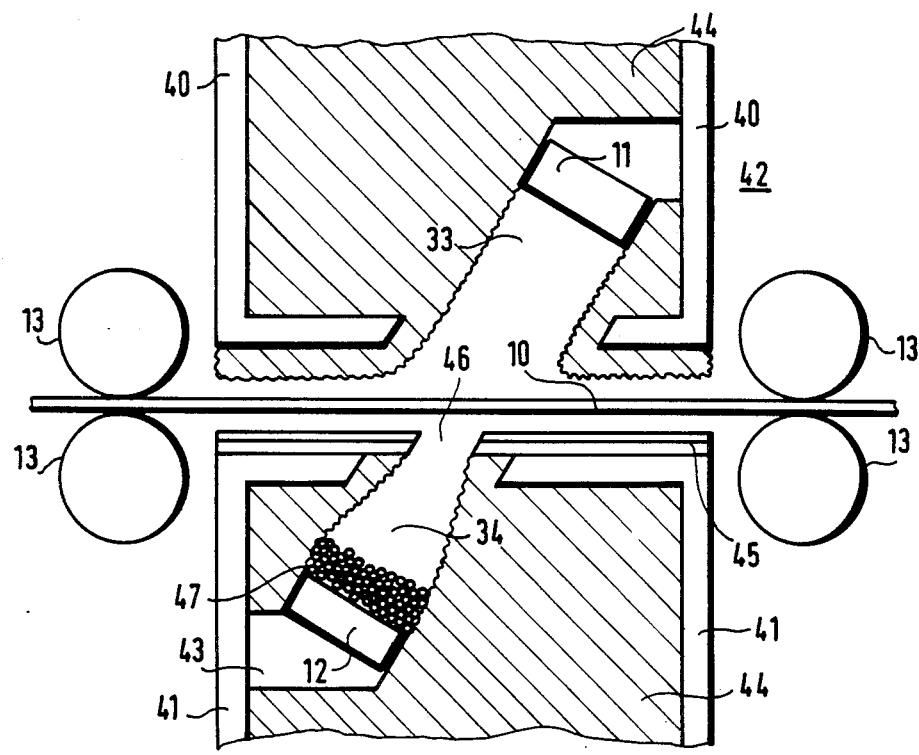
Figure 4:
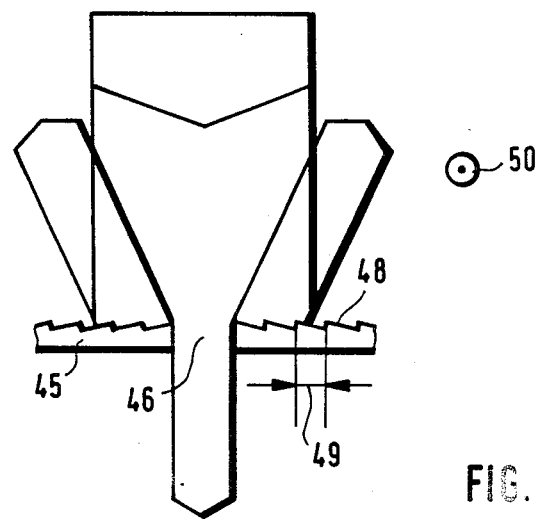

These show:

FIG. 1 a schematic view of an apparatus for determining the weight per unit area of sheet-like material FIG. 2 the arrangement of the inventive apparatus in a housing FIG. 3 a further embodiment with an additional constriction of the aperture of the beam FIG. 4 a plate for constricting the bundle of rays in cross-section FIG. 5 a schematic view of an apparatus in the reflection arrangement FIG. 1 shows a schematic view of an example of the inventive apparatus. The material to be measured 10, for example a sheet of paper, is moved by means of guide elements 13 such as the driving rollers indicated in the Figure, through between transmitter 11 and receiver 12. Transmitter 11 and receiver 12 are arranged relative to guide elements 13 in such a way that the sound radiated by the transmitter in the direction of arrow 14 hits the material to be measured 10 at an angle 17 other than 0, relative to the vertical 18 in the point of impingement of sound wave 14.

The direction of the reflected portion of sound, indicated by arrow 16, is determined by the reflection condition (angle of incidence 17 equals angle of reflection 19). Since angle of incidence 17 is other than 0, i.e. not the result of vertical exposure, according to the invention, sound wave 16 reflected on the material to be measured is directed past transmitter 11. Appropriate measures, for example an apparatus 20 with a sound-absorbing effect (sound trap), ensure that sound wave 16 cannot return to the original path of rays between the transmitter and the receiver. The sound trap may, for example, be a hollow body provided with an opening, which is lined on the inside with sound-absorbing material 28. Sound which enters through the opening is absorbed to a large extent by sound-absorbing material 28; non-absorbed sound is reflected, but remains in the interior of the cavity and is finally absorbed as well. It has turned out in practice that the mere use of a sound-absorbing material, for example a piece of foamed material, instead of the "sound-absorbing cavity", provides good results. It is also possible to dispense with sound-absorbing means 20 and direct sound 16 reflected on the material to be measured in such a way, due to an appropriate arrangement of the elements or to additional devices, such as sound mirrors, that sound 16 is reflected past the transmitter into the free space, thereby being lost. A hole in a housing wall, for example, acts in the same way as an ideal absorbant material at the same place.

The portion of sound 15 transmitted by material to be measured 10 hits receiver 12, is partly absorbed by the latter and converted into an electrical measuring signal. The non-absorbed reflected portion of sound is indicated in FIG. 1 by arrow 21. Receiver 12 is generally arranged opposite the direction of the impinging sound wave 15 in such a way that the sound wave 21 reflected on the receiver has a direction differing from the impinging wave 15. This prevents superposition between the wave 14 or 15 radiated by the transmitter and the reflected wave 21, which could lead to stationary waves. This also prevents sound wave 21 from returning to the transmitter, being reflected on it and again hitting the receiver. In each case the measuring signal and thus the determination of weight per unit area could be falsified.

Sound wave 21 reflected away from the path of rays between transmitter and receiver is either absorbed by a sound trap directly, i.e. before hitting the material to be measured, or again hits the material to be measured, as shown in FIG. 1. Analogously to the above embodiments, a portion 22 of sound wave 21 is transmitted by the material to be measured and the remaining portion 23 is reflected, the law of reflection (angle of incidence 24 equals angle of reflection 25) again determining the direction of the reflected sound wave 23. Sound traps 26, 27 absorb sound waves 22, 23 which are of no significance for the measurement and could only lead to interfering signals.

The slanted position of the receiver with respect to the impinging sound wave 15 makes angles 17 and 24 different, whereby angle 24 may be larger or smaller than angle 17 depending on the slant of the receiver.

In cases in which the material to be measured only exhibits small degrees of transmission (e.g. paper, transmission in the range of a few %), the transmitter and the receiver may be arranged parallel without falsifying the measuring result. Due to the low transmission, the influence of the sound wave 21 reflected on the receiver, which, when the transmitter and the receiver are arranged parallel, returns to the transmitter, is reflected by the latter and reaches the receiver a second time, is utterly negligible (smaller than $10^{-5}$ at an assumed transmission of 2%).

The sound wave 21 reflected on the receiver is reflected back into the original path of rays when the transmitter/receiver arrangement is not on a slant, but it does not have any influence on the measuring signal since the sound wave 23 is deflected by the reflection on the material to be measured in such a way that wave 23 can no longer reach the receiver. In this case angles 17 and 24 are equal. The superposition of impinging wave 15 and wave 21 reflected on the receiver leads to a stationary wave between the receiver and the material to be measured. The impinging and the reflected wave superimpose each other without having any mutual influence as long as there is no refraction of impinging wave 15 on the density fluctuations of the air generated by the stationary wave. With the sound pressures used, however, this case of self-refraction is very remote.

The size of angles 17 and 24 is freely selectable within wide limits, for example, 10° to 60° and may be adapted to the particular conditions at hand, for example the geometrical dimensions of a housing. Attention must be paid to the fact that, when the diameter of the bundle of sound radiated by the transmitter is given, the exposed surface on the material to be measured is larger in the case of oblique exposure as compared to vertical exposure. For large local resolution, angle 17 will therefore generally be selected so as to be small. Good measuring results have been obtained in practice with an angle 17 of 22.5°.

FIG. 2 shows how the method of determining weight per unit area as shown schematically in FIG. 1 can be applied in practice to measure paper. Since the transmission for paper generally assumes very small values, the transmitter and the receiver could be set up parallel to each other for the above-stated reasons. Transmitter 11 and receiver 12 are generally disposed in housings 31, 32 on each side of the material to be measured, in order to protect and fasten them. The two housings may be jointly attached to a base plate. The shape and/or the get-up of the housings must be such that the sound waves reflected on the material to be measured do not return to the original path of rays and in particular not to the receiver, due to the repeated reflection on the housing, in order that the measuring signal not be falsified. This can be obtained, for example, by incorporating absorbant sound traps at those points onto which the sound waves are reflected. In FIG. 2 two channels 35, 36 are provided in the direction of the reflected transmitter and receiver sound portions, which the sound may enter. The cross-sections of channels 35, 36 are preferably somewhat larger than the cross-sections of channels 33, 34 which lead directly from the transmitter to the receiver. This ensures that the entire sound radiated conically by the transmitter and reflected by the material to be measured enters the particular channel. At the end of channels 35, 36 there is sound-absorbing material 30.

Open-cell polyurethane foamed plastic has proved to be a particularly effective material in practice. The cavities in this foam are in the range of 1 mm and are thus comparable with the wavelength of the supersonics used, which is about 1.5 mm at 200 kHz. In special cases the end of the sound trap may be formed by pyramid-shaped sound absorbers, as are known, for example, for low-reflection (anechoic) rooms.

The sound-conducting channels 33–36 may be made of the housing material itself (for example, milled or bored into aluminum), but preferably the channels for conducting the sound will also be provided with sound-absorbing material. This means that only the direct sound wave radiated in a narrow cone reaches the receiver, while reflections on the walls of the sound-conducting channels are suppressed.

Guide elements 13 are arranged outside the transmitter and receiver housing so that housings 31, 32 come close to the material to be measured, thereby forming only a narrow gap. This means that disturbances (for example, general noise) from outside the measuring apparatus have no, or very little, influence on the measurement, on the one hand, and that the sound of the measuring apparatus cannot penetrate outside and in turn create disturbances, on the other hand. Furthermore, contamination of the apparatus can be reduced by the narrow gap.

FIG. 3 shows a further embodiment as may be used for determining the weight per unit area of banknotes, for example. The basic arrangement of the transmitter, receiver and material to be measured is already known from the two preceding figures and will no longer be described in detail. The same elements are provided with the same positional references in the figures. The transmitter housing comprises an appropriately shaped, stable housing wall 40, for example made of aluminum. Sound transmitter 11 is attached to a carrier 42 connected to the housing wall 40. Housing wall 40 exhibits an opening in an appropriate place for the transmitter sound to exit through. The interior of the transmitter housing is partially or, as in shown in FIG. 3, entirely lined with sound-absorbing material. The sound channel 33 leading away from the transmitter is formed by a sound-absorbing material 44 or is lined with this material.

It has turned out in practice that no separate channel (as shown by 35 in FIG. 2) must be provided for the portion of sound reflected on the material to be measured when the transmitter housing, as shown in FIG. 3, is also provided with sound-absorbing material of sufficient thickness at the outer places which reflected portions of sound can hit.

The same design of the housing is basically provided for the receiver side as for the transmitter side, i.e. with housing wall 41, carrier 43 for receiver sound transducer and sound-absorbing material 44. A plate 45 is also shown in FIG. 3, having an opening 46 which is smaller than the diameter of the sound cone radiated by the transmitter. The purpose of this plate 45 is to reduce the cross-section of the sound bundle coming from the transmitter, which is responsible for local resolution, in the vicinity of the material to be measured. This is necessary in particular when the transmitter or the receiver cannot be reduced at will due to its construction. It is well known that the diameter and the wavelength of supersonic transducers are proportional to each other within certain limits. By using plate 45, the local resolution of the apparatus can thus be increased by reducing the plate opening 46 independently of the diameter of the sound transducer. In the example shown, plate 45 is made of aluminum, for example. Means must be provided for this case for absorbing the sound hitting the plate or fading it out of the path of rays between the transmitter and the receiver. Apart from coating the plate with sound-absorbing material, the plate may be designed in such a way that impinging portions of sound are reflected away from the measuring channel. The mode of functioning of such a plate shall be described in more detail in connection with FIG. 4.

Further, a sound-absorbing layer 47 is provided on the side of the receiver sound transducer facing the transmitter. This layer serves the purpose of reducing the portion of sound reflected by the receiver. This means, on the one hand, that as little sound energy as possible is reflected by the receiver back to the side of the plate 45 facing the housing interior, which is of advantage in particular when the opening in plate 45 is smaller than the diameter of the sound transducer. On the other hand, one is better able to adapt the sound resistance of air and that of the sound transducer.

A further advantage of the layer 47 provided on the receiver sound transducer becomes apparent when material which transmits well is being measured. When the material to be measured has high transmission values, superposition of the sound wave reflected by the receiver with the sound wave radiated by the transmitter occurs when the active surfaces of the transmitter and receiver are arranged parallel (as in FIGS. 2 and 3, for example). When there is a suitable relationship between the frequency and the transmitter-receiver distance, i.e. a suitable phase relation of the waves travelling to and from the receiver, stationary waves may form between the transmitter and the receiver. The transmission of the material to be measured varies between a maximum and a minimum value depending on whether the material to be measured is located in a vibration node or an antinode of the stationary wave. The difference in the two extreme values crucially depends on the reflection factors of the elements involved (the transmitter, receiver and material to be measured). The smaller the reflection factors are, the less difference there is between the maximum and the minimum values. Therefore, in order to eliminate sensitivity to displacements of the material to be measured on the connecting line between the transmitter and the receiver, it is useful to select the reflection values of the elements involved so as to be as small as possible. Since the reflection factor of the material to be measured is given, only the reflection factors of the transmitter and receiver may be varied. However, no additional sound-absorbing material will be provided on the sound transducer, on the transmitter side, since this would reduce the sound energy radiated by the transmitter and thus the signal/noise ratio. On the receiver side, though, the addition of sound-absorbing material does not have any effect on the signal/noise ratio since both the measuring sound wave and noise are diminished to the same extent and the signal/noise ratio not affected.

The use of sound-absorbing material 47 on the active surface of the receiver has the further advantage that interference between the transmitter and the receiver can be avoided, or rather its effects reduced, with 100% alignment of the transmitter/receiver arrangement, i.e. without any material to be measured in between. If there were no sound-absorbing material 47, stationary waves could form between the transmitter and the receiver when the distance between them is a multiple of half the sound wavelength. Stationary waves disturb the measuring signal and should therefore be avoided.

A thin layer of the above-mentioned open-cell polyurethane foam has proved useful as sound-absorbing material 47 to be provided on the sound receiver. A thin layer of a needled felt coating is also suitable.

In the apparatus shown in FIG. 3, the reflection of the sound wave reflected by the receiver on plate 45 is reduced further by having the plate be coated on the side facing the housing interior with sound-absorbing material. When a plate 45 with a small opening relative to the diameter of the sound transducer is used, the sound channel between opening 46 in plate 45 and the receiver may preferably have a conical design, as shown in FIG. 3.

Instead of completely filling in the cavity formed by the housing wall with sound-absorbing material on the receiver side, as shown in FIG. 3, it is also possible to provide only the necessary areas, i.e. in particular sound channel 34 and the underside of plate 45 in the area of opening 46, with sound-absorbing material 30.

FIG. 4 shows plate 45 in cross-section. The cross-section is on a plane perpendicular to the plane of projection of FIG. 3, i.e. one has the view of FIG. 4 when looking at the plate in direction of movement 50 of the material to be measured. The impinging transmitter sound has a diameter which is essentially given by the sound transducer. Plate 45 has an opening 46 to constrict the cross-section of the bundle. Behind the plate the sound bundle has a smaller diameter, thereby allowing for higher local resolution.

The upper side of the plate, which faces the impinging sound, is designed in such a way that the sound which does not go through opening 46 is reflected away from the measuring plane formed by the vertical 18 and transmitter sound 14 (and which is at right angles to the plane of projection in FIG. 4). In the most simple case, this is achieved by an inclined surface of the plate. The disadvantage when there is only one inclined surface (e.g. conical or similar to a gable roof) is that the plate has a relatively thick design in the area of the opening and a relatively thin design at the edges if a large reflection angle acceptable in practice is required. It is more advantageous to divide it into several areas, as shown in FIG. 4. The sound is reflected away from the direction of incidence under conditions of reflection on the various small slanted areas 48.

When the wavelength of the sound wave is approximately as large as distance 49 between adjacent areas 48, diffraction phenomena also occur.

Since various points on plate 45 may be regarded as independent sound transmitters, there are preferred directions, so-called "diffraction patterns", in which the sound waves interfere positively, due to the phase relation of the punctiform transmitters with respect to each other. When the direction of a diffracted wave coincides with the direction of reflection, the efficiency of the sound energy diffracted away from the impinging ray is increased. This case of high efficiency may be obtained by adapting the distances 49 to the slanted position of areas 48, or vice versa.

The inventive slanted position of the elements in combination with additional means which prevent reflected portions of sound from returning to the path of rays between the transmitter and the receiver may also be advantageously used for reflection measurement. A schematic view of such an apparatus is shown in FIG. 5. Identical elements are provided with the same positional references as in the preceding figures.

In reflection measurement, sound 14 emerging from transmitter 11 hits material to be measured 10 at an angle 17. A portion 15 of the transmitter sound is transmitted by the material to be measured; the remaining portion which is not absorbed by the material to be measured is reflected in direction 16 at an angle 19 due to the law of reflection and hits receiver 12. The active surface of receiver 12 is inclined relative to the direction of the approaching sound wave 16 in such a way that the direction of sound wave 21 reflected on the receiver deviates from the direction of the approaching sound wave 16. A sound trap 29 absorbs the portion of sound reflected on the receiver.

Since sound portion 21 reflected on the receiver can no longer return to the path of rays serving for measurement, which is given by the directions of sound waves 14 and 16, no disturbing interference occurs in this path of rays. Thus, stationary waves between the transmitter, the receiver and the material to be measured, which partly acts as a reflector, are avoided, for example, as are multiple reflections which are superimposed on the measuring signal proper and may falsify it.

I claim:

1. An apparatus for dynamically determining localized weight per unit area of sheet-like material, for example, paper comprising:
    a sound transmitter element spaced from the sheet-like material and emitting sound waves for application to the sheet-like material;
    a receiver element for receiving the portion of the sound waves transmitted and/or reflected by the sheet-like material as a measuring signal;
    measuring means coupled to said receiver element for determining the weight per unit area from the sound wave portions received by said receiver element;
    said transmitter element, said receiver element, and the sheet-like material being arranged at angles relative to each other such that substantially none of the sound waves reflected by the sheet-like material return to the element from which they came; and
    means for preventing reflected sound waves not forming part of said measuring signal from reentering the path of the sound waves between said receiver and transmitter elements.

2. The apparatus as in claim 1 wherein the prevention means is means having a sound-absorbing effect.

3. The apparatus as in claim 2 wherein the means having a sound-absorbing effect is made of sound-absorbing foamed material.

4. The apparatus as in claim 1 wherein the prevention means is a sound reflector which conducts the otherwise returning sound waves into free space.

5. The apparatus as in claim 1 wherein the transmitter element is a continuously operated supersonic transmitter.

6. The apparatus as in claim 1 wherein the transmitter and receiver elements are arranged opposite one another and an imaginary connecting line between the transmitter and receiver elements forms an angle approximately between 10° and 60°, preferably 22.5°, with the vertical through the material to be measured.

7. The apparatus as in claim 6 wherein the active surface of the receiver element is arranged at right angles with respect to the imaginary connecting line between the transmitter and receiver elements and is provided with sound-absorbing material, for example open-cell polyurethane foam or a needled felt coating.

8. The apparatus as in claim 6 wherein the active surface of the receiver is on a slant with respect to the imaginary connecting line between the transmitter and receiver.

9. The apparatus as in claim 1 wherein said receiver element is so arranged that the sound waves transmitted through the sheet-like material are reflected off said receiver element in a direction outside the path of the sound waves between said receiver and transmitter elements.

* * * * *